US011393557B2

(12) United States Patent
Sanborn

(10) Patent No.: US 11,393,557 B2
(45) Date of Patent: Jul. 19, 2022

(54) SYSTEMS AND METHODS FOR HIGH-ACCURACY VARIANT CALLING

(71) Applicant: Nantomics, LLC, Culver City, CA (US)

(72) Inventor: John Zachary Sanborn, Santa Cruz, CA (US)

(73) Assignee: NantOmics, LLC, Culver City, CA (US)

(*) Notice: Subject to any disclaimer, the term of this patent is extended or adjusted under 35 U.S.C. 154(b) by 417 days.

(21) Appl. No.: 15/755,095

(22) PCT Filed: Aug. 25, 2016

(86) PCT No.: PCT/US2016/048768
§ 371 (c)(1),
(2) Date: Feb. 26, 2018

(87) PCT Pub. No.: WO2017/035392
PCT Pub. Date: Mar. 2, 2017

(65) Prior Publication Data
US 2018/0237949 A1    Aug. 23, 2018

Related U.S. Application Data

(60) Provisional application No. 62/209,858, filed on Aug. 25, 2015.

(51) Int. Cl.
G01N 33/48    (2006.01)
G16B 30/00    (2019.01)
G16B 35/00    (2019.01)
G16C 20/60    (2019.01)
G16B 45/00    (2019.01)
G16B 50/00    (2019.01)
G16B 20/00    (2019.01)
G16B 30/10    (2019.01)
G16B 20/40    (2019.01)
G16B 20/20    (2019.01)
G06G 7/58     (2006.01)

(52) U.S. Cl.
CPC ............ G16B 30/00 (2019.02); G16B 20/00 (2019.02); G16B 20/20 (2019.02); G16B 20/40 (2019.02); G16B 30/10 (2019.02); G16B 35/00 (2019.02); G16B 45/00 (2019.02); G16B 50/00 (2019.02); G16C 20/60 (2019.02)

(58) Field of Classification Search
None
See application file for complete search history.

(56) References Cited

U.S. PATENT DOCUMENTS

2013/0267429 A1    10/2013    Gardner et al.
2014/0114579 A1    4/2014     Royce et al.
2014/0114584 A1    4/2014     Bruestle
2014/0228223 A1    8/2014     Gnirke et al.
2015/0110754 A1    4/2015     Bai et al.
2015/0342975 A1    12/2015    Geyer et al.
2016/0089388 A1    3/2016     Levitt

FOREIGN PATENT DOCUMENTS

| AU | 2016311444 A1 | 3/2018 |
|----|---------------|--------|
| AU | 2016311444 B2 | 2/2019 |
| AU | 2019201869 A1 | 4/2019 |
| CA | 2 996 702 A1  | 3/2017 |
| CN | 102460155 A   | 5/2012 |
| CN | 103699819 A   | 4/2014 |
| CN | 108351917 A   | 7/2018 |
| CN | 111225673 A   | 6/2020 |
| IL | 257724 A      | 11/2018 |
| JP | 2015-35212    | 2/2015 |
| JP | 2018-533111 A | 11/2018 |
| JP | 2019-169177 A | 10/2019 |
| KR | 10-2018-0058718 A | 6/2018 |
| KR | 10-2019-0090022 A | 7/2019 |
| MX | 2018002293 A  | 9/2018 |
| RU | 2018 106 934 A | 9/2019 |
| WO | 2010127045    | 11/2010 |
| WO | 2010/127045 A3 | 1/2011 |
| WO | 2014/116729 A2 | 7/2014 |
| WO | 2015/095811 A2 | 6/2015 |
| WO | 2016/164833 A1 | 10/2016 |
| WO | 2017/035392 A1 | 3/2017 |
| WO | 2017/143092 A1 | 8/2017 |
| WO | 2017/161360 A4 | 11/2017 |
| WO | 2018/005973 A1 | 1/2018 |
| WO | 2019/050926 A1 | 3/2019 |

OTHER PUBLICATIONS

Boegel, Sebastian, et al. "HLA typing from RNA—Seq sequence reads." Genome medicine, 2013, 4(12): 102.
Browning M. J. et al. "Tissue typing the HLA-A locus from genomic DNA by sequence-specific PCR: comparison of HLA genotype and surface expression on colorectal tumor cell lines." Proceedings of the National Academy of Sciences, 1993, 90(7): 2842-2845.
Laehnemann D. et al., "Denoising DNA deep sequencing data—high-throughput sequencing errors and their correction." Briefings in bioinformatics, 2016 (Advance Access Publication Date: May 29, 2015), 17(1): 154-179.
ISA/KR, International Search Report and Written Opinion, completed Dec. 21, 2016 for PCT Application No. PCT/US2016/048768, 14 pages.

(Continued)

Primary Examiner — Eric S Dejong
(74) Attorney, Agent, or Firm — Martin Fessenmaier; Umberg Zipser LLP

(57) ABSTRACT

Systems and methods for in silico prediction of HLA type of a patient are presented in which patient sequence reads and a reference sequence with known and distinct HLA alleles are used in a de Bruijn graph. A composite match score is then used to rank HLA alleles, thus providing a first HLA type. A second HLA type is identified by re-ranking using an adjusted composite match score.

20 Claims, 2 Drawing Sheets

(56) References Cited

OTHER PUBLICATIONS

Dilthey el al., 'Improved genome inference in the MHC using a population reference graph' Nature Genetics, vol. 47, No. 6, pp. 682-688 (Jun. 2015).
Iqbal et al., 'De novo assembly and genotyping of variants using colored de Bruijn graphs' Nature Genetics, vol. 44, No. 2, pp. 226-232 (2012).
Koren et al., 'Hybrid error correction and de novo assembly of single-molecule sequencing reads' Nature Biotechnology, vol. 30, No. 7, pp. 693-700 (2012).
Wang et al., 'High-throughput, high-fidelity HLA genotyping with deep sequencing' PNAS, vol. 109, No. 22, pp. 8676-8681 (2012).
Rimmer et al. 'Integrating mapping-, assembly- and haplotype-based approaches for calling variants in clinical sequencing applications' Nature Genetics, \lol .46, No. 8, pp. 912-918 (2014).
Iqbal, Z., De novo assembly and genotyping of variants using colored de Bruijn graphs, Supplementary Note, Nature Genetics, (32 pages).
Bai, Y., et al., Inference of high resolution HLA types using genome-wide RNA or DNA sequencing reads, BMC Genomics 2014 pp. 1-16.
Koboldt et al., "VarScan 2: Somatic Mutation and Copy Number Alteration Discovery in Cancer by Exome Sequencing", Cold Spring Harbor Laboratory Press, www.genome.cshlp.org, Jan. 11, 2012.
Compeau et al., "How to Apply de Bruijn Graphs to Genome Assembly", Nature Biotechnology, vol. 29, No. 11, Nov. 2011, pp. 987-991.
Wajid et al., "Review of General Algorithmic Features for Genome Assemblers for Next Generation Sequencers", Genomics Proteomics Bioinformatics 10, 2012 pp. 58-73.
Song, K. et al., 'New developments of alignment-free sequence comparison: measures, statistics and next-generation sequencing', Briefings in bioinformatics, 2013, vol. 15, No. 3, pp. 343-353.
Kotamarti et al., "Analyzing Taxonomic Classification Using Extensible Markov Models", Bioinformatics Original Paper, vol. 26 No. 18 2010, pp. 2235-2241.
Xia et al., "Biggie: A Distributed Pipeline for Genomic Variant Calling", Division of Computer Science, University of California, Berkeley.
Office Action received in Russian Patent Application Serial No. 2018106934/10(010650) dated May 26, 2020, 21 pages (Including English Translation).
Communication pursuant to Article 94(3) EPC received for European Patent Application Serial No. 16840152.9 dated Aug. 19, 2020, 8 pages.
Requirement for Restriction/Election received for U.S. Appl. No. 16/640,336 dated Sep. 18, 2020, 11 pages.
Hughes (Cancer Therapy Advisor, Jan. 16, 2014, "Vaccine Combination Improves Survival in Metastatic Pancreatic Cancer", online at https://www.cancertherapyadvisor.com/home/news/conference-coverage/gastrointestinal-gi-cancers-symposium/gi-cancers-symposium-2014/vaccine-combination-improves-survival-in-metastatic.
Notification of Reason for Refusal received for Japanese Patent Application Serial No. 2019-095951 dated Aug. 4, 2020, 6 pages (Including English Translation).
Li et al., "The Sequence Alignment/Map format and SAMtools", Bioinformatics, 2009, vol. 25, No. 16, pp. 2078-2079.
Examination report No. 1 received for Australian Patent Application Serial No. 2016311444 dated Jun. 7, 2018, 5 pages.
Examination report No. 1 received for Australian Patent Application Serial No. 2016311444 dated Oct. 1, 2018, 4 pages.
Notice of acceptance received for Australian Patent Application Serial No. 2016311444 dated Jan. 24, 2019, 3 pages.
Examination report No. 1 received for Australian Patent Application Serial No. 2019201869 dated Mar. 4, 2020, 4 pages.
Office Action received for Canadian Patent Application Serial No. 2996702 dated Mar. 29, 2018, 5 pages.

Office Action received for Canadian Patent Application Serial No. 2996702 dated Nov. 15, 2018, 4 pages.
Office Action received for Canadian Patent Application Serial No. 2996702 dated Sep. 11, 2019, 5 pages.
Office Action received for Canadian Patent Application Serial No. 2996702 dated Mar. 11, 2020, 4 pages.
Extended European Search Report received for European Patent Application Serial No. 16840152.9 dated Sep. 4, 2018, 11 pages.
Office Action Received for Russian Patent Application Serial No. 2018106934 dated Oct. 22, 2019, 5 pages.
Office Action Received for Israel Patent Application Serial No. 263115 dated Feb. 12, 2019, 2 pages.
Notice of Reasons for Refusal received for Japanese Patent Application Serial No. 2018510056 dated Jul. 24, 2018, 6 pages (Including English Translation).
Notice of Reasons for Refusal received for Japanese Patent Application Serial No. 2018510056 dated Oct. 23, 2018, 6 pages (Including English Translation).
Decision to Grant received for Japanese Patent Application Serial No. 2018510056 dated Apr. 23, 2019, 5 pages (Including English Translation).
Notification of Reason for Refusal received for Korean Patent Application Serial No. 1020187008056 dated Jan. 28, 2019, 6 pages (Including English Translation).
Notification of Reason for Refusal received for Korean Patent Application Serial No. 1020197020554 dated Feb. 17, 2020, 6 pages (Including English Translation).
International Preliminary Report on Patentability Chapter I received for PCT Application Serial No. PCT/US2016/048768 dated Mar. 8, 2018, 9 pages.
Office Action Received for Russian Patent Application Serial No. 2018106934 dated May 23, 2019, 3 pages.
International Search Report Received for Brazilian Patent Application Serial No. 112018003631 dated Mar. 17, 2020, 6 pages.
Zerbino et al., "Velvet: Algorithms for de novo short read assembly using de Bruijn graphs", Cold Spring Harbor Laboratory Press, vol. 18, pp. 821-829.
Compeau Phillip E. C., "Why are de Bruijn graphs useful for genome assembly?", Nat Biotechnol., vol. 29, No. 11, pp. 987-991.
Notification of Reason for Refusal received for Korean Patent Application Serial No. 1020187008056 dated Sep. 18, 2018, 6 pages (Including English Translation).
Xia et al., "BIGGIE: A Distributed Pipeline for Genomic Variant Calling", Division of Computer Science, 2012, pp. 1-9.
Szeto et al., "Building patient-specific predictors of drug responses from cell line genomics", Nantomics, 2015, 1 page.
Malyshev et al., "Generalized graphs of de Bruin", Mathematical Notes, 1997, vol. 62, No. 4, pp. 449-456.
Sergushichev et al., "Combining de Bruijn graphs, overlap graphs and microassembly for de novo genome assembly", Ser. Math. Mech. Inform., 2013, vol. 13, No. 2, pp. 51-57.
Office Action Received for Russian Patent Application Serial No. 2018106934 dated Dec. 26, 2018, 12 pages (Including English Translation).
Hui-Chou et al., "Short-term application of doxorubicin chemotherapy immunosuppressive side effects for composite tissue allotransplantation", Annals of Plastic Surgery, Feb. 2012, vol. 68, No. 2, pp. 215-221.
Park et al., "Doxorubicin enhances CD4+ T-cell immune responses by inducing expression of CD40 ligand and 4-1BB" International Immunopharmacology, 2009, vol. 9, pp. 1530-1539.
Hannesdóttir et al., "Lapatinib and doxorubicin enhance the Stat1-dependent antitumor immune response", Eur. J. Immunol., 2013, vol. 43, pp. 2718-2729.
Han et al., "IL-15:IL-15 receptor alpha superagonist complex: high-level co-expression in recombinant mammalian cells, purification and characterization", Cytokine, 2011, vol. 56, pp. 804-810.
International Search Report and Written Opinion received for PCT Application Serial No. PCT/US2018/049518 dated Dec. 24, 2018, 14 pages.
Chawla et al., "First-Line Aldoxorubicin vs Doxorubicin in Metastatic or Locally Advanced Unresectable Soft-Tissue Sarcoma: A Phase 2b Randomized Clinical Trial", Jama Oncology, 2015, vol. 1, No. 9, pp. 1272-1280.

(56) References Cited

OTHER PUBLICATIONS

Mittal et al., "New insights into cancer immunoediting and its three component phases-elimination, equilibrium and escape", Current Opinion in Immunology, Apr. 2014, vol. 27, pp. 16-25.
Chen et al., "Bioinspired Nano-Prodrug with Enhanced Tumor Targeting and Increased Therapeutic Efficiency", Small, 2015, vol. 11, No. 39, pp. 5230-5242.
International Preliminary Report on Patentability received for PCT Application Serial No. PCT/US2018/049518 dated Mar. 19, 2020, 11 pages.
Pang et al., "Drug-induced histone eviction from open chromatin contributes to the chemotherapeutic effects of doxorubicin", Nature Communications, 2013, vol. 4, No. 1908, pp. 1-13.
Wick et al., "Pathway inhibition: emerging moleculartargets for treating glioblastoma", Neuro-Oncology, 2011, vol. 13, No. 6, pp. 566-579.
Silber et al., "O6-methylguanine-DNA methyltransferase in glioma therapy:Promise and problems", Biochim Biophys Acta, Aug. 2012, vol. 1826, No. 1, 24 pages.
Stupp et al., "Radiotherapy plus Concomitantand Adjuvant Temozolomide for Glioblastoma", The New England journal of Medicine, Mar. 10, 2005, vol. 352, No. 10, pp. 987-996.
Stupp et al., "Effects of radiotherapy with concomitant and adjuvant temozolomide versus radiotherapy alone on survival in glioblastoma in a randomised phase III study: 5-year analysis of the EORTC-NCIC trial", Lancet Oncology, 2009, vol. 10, pp. 459-466.
Oliva et al., "Acquisition of Temozolomide Chemoresistance in Gliomas Leads to Remodeling of Mitochondrial Electron Transport Chain", The Journal of Biological Chemistry, Dec. 17, 2010, vol. 285, No. 51, pp. 39759-39767.
Soda et al., "Mechanisms of Neovascularization and Resistance to Antiangiogenic Therapies in Glioblastoma Multiforme", Journal of Mol. Med., Apr. 2013, vol. 91, No. 4, 17 pages.
Chamberlain Marc C., "Bevacizumab for the Treatment of Recurrent Glioblastoma", Clinical Medicine Insights: Oncology, 2011, vol. 5, No. 117-129.
Weller et al., "Standards of care for treatment of recurrent glioblastoma—are we there yet?", Neuro-Oncology, 2013, vol. 15, No. 1, 24 pages.
Misra et al., "Drug delivery to the central nervous system: a review", J. Pharm. Pharmaceut Sci., 2003, vol. 6, No. 2, pp. 252-273.
Holst et al., "Uptake of Adriamyein in Tumour and Surrounding Brain Tissue in Patients withMalignant Gliomas", Acta Neurochirurgica, 1990, vol. 104, pp. 13-16.
Chen et al., "Lactoferrin modified doxorubicin-loaded procationic liposomes for the treatmentof gliomas", European Journal of Pharmaceutical Sciences, 2011, vol. 44, pp. 164-173.
Beier et al., "RNOP-09: Pegylated liposomal doxorubicine and prolonged temozolomide in addition to radiotherapy in newly diagnosed glioblastoma—a phase II study", BMC Cancer, 2009, vol. 9, No. 308, pp. 1-10.
Ananda et al., "Phase 2 trial of temozolomide and pegylated liposomal doxorubicin in thetreatment of patients with glioblastoma multiforme following concurrent radiotherapy and chemotherapy", Journal of Clinical Neuroscience, 2011, vol. 18, pp. 1444-1448.
Kratz et al., "Probing the Cysteine-34 Position of Endogenous Serum Albumin with Thiol-Binding Doxorubicin Derivatives. Improved Efficacy of an Acid-Sensitive Doxorubicin Derivative with Specific Albumin-Binding Properties Compared to That of the Parent Compound", J. Med. Chem., 2002, vol. 45, pp. 5523-5533.
Ingelheim et al., "INNO-206, the (6-maleimidocaproyl hydrazone derivative of doxorubicin), shows superior antitumor", Invest New Drugs, 2010, vol. 28, pp. 14-19.
Kratz et al., "Combination therapy with the albumin-binding prodrug of doxorubicin (INNO-206) and doxorubicin achieves complete remissions and improves tolerability in an ovarian A2780 xenograft model", Invest New Drugs, 2012, vol. 30, No. 1, pp. 1743-1749.

Unger et al., "Phase I and Pharmacokinetic Study of the (6-Maleimidocaproyl)Hydrazone Derivative of Doxorubicin", Clinical Cancer Research, 2007, Aug. 15, 2007, vol. 13, No. 16, 4858-4866.
Ohlfest et al., "Combinatorial Antiangiogenic Gene Therapy by Nonviral Gene Transfer Using the Sleeping Beauty Transposon Causes Tumor Regression and Improves Survival in Mice Bearing Intracranial Human Glioblastoma", Molecular Therapy, Nov. 2005, vol. 12, No. 5, pp. 778-788.
Roti et al., "Acute Doxorubicin Insult in the Mouse Ovary Is Cell- and Follicle-Type Dependent", Plos One, Aug. 2012, vol. 7, No. 8, pp. 1-19.
Carvalho et al., "Doxorubicin: The Good, the Bad and the Ugly Effect", Current Medicinal Chemistry, 2009, vol. 16, pp. 3267-3285.
Kratz Felix et al., "Albumin as a drug carrier: Design of prodrugs, drug conjugates and nanoparticles", Journal of Controlled Release, 2008, vol. 132, pp. 171-183.
Maeda et al., "Tumor vascular permeability and the EPR effect in macromolecular therapeutics: a review", Journal of Controlled Release, 2000, vol. 65, No. 271-284.
Kratz Felix, "DOXO-EMCH (INNO-206): the first albumin-binding prodrug of doxorubicin to enter clinical trials", Expert Opinion on Investigational Drugs, 2007, vol. 16, No. 6, pp. 855-866.
Chawla Sant et al., "Phase 3 Study of Aldoxorubicin vs Investigator's Choice as Treatment for Relapsed/Refractory Soft Tissue Sarcomas" Asco Annual Meeting, 2017, 24 pages.
Fritz et al., "Administration of aldoxorubicin and 14 days continuous infusion of ifosfamide/Mesna in metastatic or locally advanced sarcomas", Cytrx Corporation, 1 page.
Sanchez et al., "Anti-Myeloma Effects of the Novel Anthracycline Derivative INNO-206", Clinical Cancer Research, 2012, vol. 18, No. 3856-3867.
Chawla et al., "Longer Term Cardiac Safety of Aldoxorubicin", Cyrix Corporation, 1 page.
Groves et al., "Phase 2 Study of Aldoxorubicin in Relapsed Glioblastoma", Cytrx corporation, 1 page.
Parsons et al., "Treatment of HIV-Associated Kaposi's Sarcoma with Aldoxorubicin", Cytrx Corporation, 1 page.
Sankhala et al., "Phase 1b Study of Aldoxorubicin + Gemcitabine in Metastatic Solid Tumors", Cytrx Corporation, 1 page.
CytRx Corporation, "Clinical Study Report INNO-206-P2-STS-01 Clinical, Statistical, and Regulatory Assessment", Hurley Consulting Associates Ltd, May 6, 2016, 10 pages.
"Kratz et al., ""Acute and repeat-dose toxicity studies of the (6-maleimidocaproyl)hydrazone derivativeof doxorubicin (DOXO-EMCH), an albuminbindingprodrug of the anticancer agent doxorubicin"", Human & Experimental Toxicology, vol. 2007, vol. 26, No. 19-35."
Lebrecht et al., "The 6-maleimidocaproyl hydrazone derivative of doxorubicin (DOXO-EMCH)is superior to free doxorubicin with respect to cardiotoxicity and mitochondrial damage", Int. J. Cancer, 2006, vol. 120, pp. 927-934.
Graeser et al., "INNO-206, the (6-maleimidocaproyl hydrazone derivative of doxorubicin), shows superior antitumor efficacy compared to doxorubicin in different tumor xenograft models and in an orthotopic pancreas carcinoma model", Springer Science, 2008, 6 pages.
Kratz et al., "Evaluation of combination therapy schedules of doxorubicin and an acid-sensitive albumin-binding prodrug of doxorubicin in the MIA PaCa-2 pancreatic xenograft model", International Journal of Pharmaceutics, 2012, 9 pages.
Mita et al., "Pharmacokinetic study of aldoxorubicin in patients with solid tumors", Ivest New Drugs 2015, vol. 33, pp. 341-348.
Marrero et al., "Therapeutic Efficacy of Aldoxorubicin in an Intracranial Xenograft Mouse Model of Human Glioblastoma", Neoplasia, Oct. 2014, vol. 16, No. 10, pp. 874-882.
"Response to FDA Request For Information: Type C Meeting Mar. 22, 2017," CytRX Corporation, Jun. 27, 2017, 118 pages.
"[14C]Doxorubicin, [doxorubicin-14-14C]Aldoxorubicin and [linker-3H]Aldoxorubicin: Synthesis and Rat ADME Package", Pharmaron, 2017, 14 pages.

(56) References Cited

OTHER PUBLICATIONS

Decision to Grant received for Japanese Patent Application Serial No. 2019095951 dated Feb. 9, 2021, 5 pages (Including English Translation).
Grant of Patent received for Korean Patent Application Serial No. 10-2019-7020554 dated Nov. 26, 2020, 4 pages (Including English Translation).
Notice of Final Rejection received for Korean Patent Application Serial No. 1020197020554 dated Oct. 28, 2020, 9 pages (Including English Translation).
Mei et al., "Cistrome Data Browser: a data portal for ChIP-Seq and chro", Nucleic Acids Research, 2016, vol. 45, pp. D658-D662.
Office Action received for Indian Patent Application Serial No. 201827007346 dated Jan. 25, 2021, 8 pages.
Notification to Grant Patent Right for Invention received for Chinese Patent Application Serial No. 201680054282.0 dated Feb. 8, 2022, 3 pages. (Including English Translation).
First Office Action received for Chinese Patent Application Serial No. 201680054282.0 dated Aug. 3, 2021, 16 pages (Including English Translation).

SYSTEMS AND METHODS FOR HIGH-ACCURACY VARIANT CALLING

This application claims priority to U.S. provisional application with the Ser. No. 62/209,858, filed Aug. 25, 2015.

FIELD OF THE INVENTION

The field of the invention is systems and methods of in silico analysis of nucleotide sequences, especially as it relates to high-accuracy calling of SNPs, multi-nucleotide variants, indels, structural variants, and HLA typing.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Variant detection for high-throughput sequencing data has become increasingly important for accurately aligning highly related genomic sequence segments that are often misaligned due to the minor changes in the sequence reads, leading either to inaccuracies or loss of variant information. Several attempts have been undertaken to improve alignment of highly related sequences. For example, "Platypus" (The Wellcome Trust Centre for Human Genetics) is a tool designed for relatively efficient and accurate variant-detection in high-throughput sequencing data. By using local realignment of reads and local assembly, Platypus achieves relatively high sensitivity and high specificity for detection of SNPs, MNPs, short indels, replacements and deletions up to several kb. While Platypus is often more accurate as traditional alignment systems, various difficulties nevertheless remain. Among other things, processing genomic data covering the entire genome is problematic, and accuracy may be less than desirable where multiple sequences with high similarity are present. Similarly, DISCOVAR (Broad Institute) is a relatively accurate tool to assemble sequences and identify variants. However, DISCOVAR is generally not suitable for processing of massive data quantities.

In another approach, Big Genomics Inference Engine (BIGGIE; *Bioinformatics*, vol. 25, pp. 2078-9, 2009), processing speed is increased by first classifying a genome into high- and low-complexity regions and subsequently allocating resources accordingly. While such approach tends to reduce demand on computational resources, variant calling is often less than desirable where variations occur in low complexity regions. In addition, most of the known variant callers for next-generation sequencing data employ a probabilistic framework (e.g., using Bayesian statistics) to detect variants and assess confidence in them. While such approach generally works satisfactorily, various factors such as extreme read depth, pooled samples, and contaminated or impure samples tend to confound analysis. To overcome such problems, VarScan (*Genome Res.* 2012 22: 568-576) employs a heuristic/statistic approach to call variants that meet desired thresholds for read depth, base quality, variant allele frequency, and statistical significance. However, such approach will generally not identify larger changes in the genome that are not spanned by a single read.

In a still further known method, a colored DeBruijn graph is generated from (*Nat Genet.* 2012; 44(2): 226-232) sequencing data using relatively long k-mers (e.g., k is at least 55) and a hash table that implicitly encodes the graph. However, for isolated SNPs, short indels (1-100 bp) and small complex combinations of SNPs and indels (1-100 bp) the authors reported only 80% power to detect heterozygous sites and 90% power to detect homozygous variant sites. Moreover, for moderate size (100-1000 bp) indels and complex variants, power is 50% and 75-80% for heterozygous and homozygous sites respectively, and for large variants (1-50 kb) the authors reported only power to detect homozygous variant sites (35%). Consequently, while a colored DeBruijn graph as described facilitates analysis of SNPs and indels to at least some degree, accuracy and detection power is less than desirable. As such, the major strength of that approach lies in the simultaneous analysis of multiple genomes, which enables powerful and accurate approaches to variant detection without any need of a reference genome.

Thus, even though numerous systems and methods for variant calling are known in the art, there remains a need for improved systems and methods for high-accuracy variant calling, especially as it relates to in silico HLA typing.

SUMMARY OF THE INVENTION

The inventive subject matter is directed to various systems, methods and devices for high-accuracy variant calling from patient sequence data, and especially as it relates to HLA typing using DNA and/or RNA sequences from sequencing machines. In especially preferred aspects, the patient sequence reads and a reference sequence comprising multiple HLA alleles are processed in a De Bruijn graph approach. Each patient sequence read provides a weighted vote for the various alleles, and the total votes for each allele are then used to rank the alleles. The topmost allele in the ranking is the first HLA-type, and a re-ranking of remaining alleles with bias against k-mer matching the first HLA-type then provides the second HLA-type.

In one aspect of the inventive subject matter, the inventor contemplates a method of in silico predicting an HLA-type for a patient in which a reference sequence is provided that includes a plurality of sequences of known and distinct HLA alleles, and in which a plurality of patient sequence reads are provided, wherein at least some of the patient sequence reads include a sequence encoding a patient specific HLA. In a further step, the patient sequence reads are decomposed into a plurality of respective sets of k-mers, and a composite de Bruijn graph is then generated using the reference sequence and the plurality of respective sets of k-mers. It is further contemplated that each of the known and distinct HLA alleles are ranked using a composite match score that is calculated from respective votes of the plurality of patient sequence reads, wherein each vote uses k-mers that match corresponding segments in the known and distinct HLA alleles.

Most typically, the reference sequence includes alleles for at least one HLA type that have an allele frequency of at least 1%, or the reference sequence includes at least ten different alleles for at least one HLA type, and/or alleles for at least two distinct HLA types. With respect to the HLA type it is contemplated that suitable HLA-types include an HLA-A type, an HLA-B type, an HLA-C type, a HLA-DRB-1 type, and/or a HLA-DQB-1 type.

Patient sequence reads will typically comprise at least one of a plurality of DNA sequencing reads and RNA sequencing reads, and will typically map to chromosome 6p21.3. Most typically, the patient sequence reads are next generation sequencing reads and further comprise metadata, and/or have a length of between 50 and 250 bases. With respect to k-mers it is contemplated that preferred k-mers will have a length of 10-20, and/or will have a length of between 5% and 15% of a length of the patient sequence read. While not limiting to the inventive subject matter, it is generally preferred that the composite match score is a sum of all votes from the plurality of patient sequence reads, wherein the vote is typically a value representing a fraction of matching k-mers to total number of k-mers per patient sequence read.

Therefore, and using the composite match score, contemplated methods may comprise a step of identifying a top-ranking HLA allele as a first HLA-type of the patient. Where desired, an additional step of re-ranking the remaining non-top-ranking known and distinct HLA alleles may be implemented using an adjusted composite match score to identify an adjusted top-ranking HLA allele as a second HLA-type of the patient. Most typically, the adjusted composite match score may be calculated from respective adjusted votes of the plurality of patient sequence reads, and the adjusted votes may be calculated by devaluing a weight of a k-mer that matches the first HLA-type.

Considering the above, the inventor therefore also contemplates a computer system for in silico predicting an HLA-type for a patient. Viewed form a different perspective, the inventor also contemplates s non-transient computer readable medium containing program instructions for causing a computer system in which a reference sequence database and a patient sequence data source are informationally coupled to an analysis engine. With respect to suitable reference sequences, patient sequence reads, HLA-types, k-mers, composite match scores, and additional re-ranking steps, the same considerations as provided above apply.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
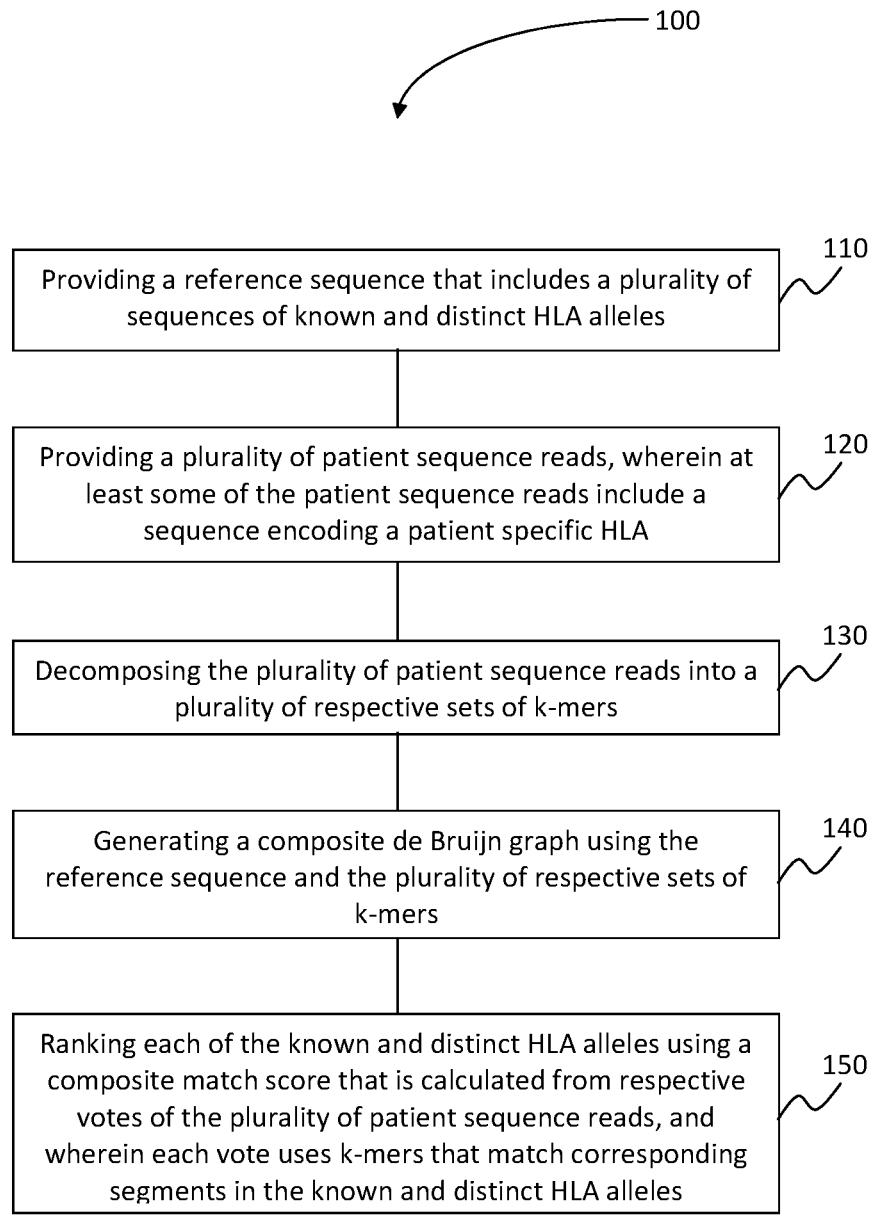
FIG. 1 is a schematic of one exemplary method according to the present inventive subject matter.

The inventor has discovered that highly accurate alignment of various closely related sequences is readily achievable in an approach in which the sequences are processed using de Bruijn graph-based methods in conjunction with a reference sequence with known sequence information, and statistical and heuristic analysis. Such analysis is particularly advantageous for HLA determination from DNA and/or RNA sequencing information since each HLA-type has numerous often very similar alleles, and as traditional alignment methods typically fail to have significant differentiation capabilities where sequences have high degree of similarity.

In one exemplary aspect of the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, www.allelefrequencies.net). Alternatively, the reference sequence may also be built from individual known HLA-alleles based on one or more pre-determined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele as is also shown in more detail below.

For identification of the second allele for the same HLA-type, the inventor discovered that even relatively similar second alleles can be resolved in a more heuristic approach where the top-ranking HLA-allele is removed from further consideration, and where the remaining alleles are re-ranked using an adjusted ("scaled") vote. More specifically, the re-ranking is performed such that the vote value for k-mers that had a match with the top-ranking allele is reduced in the re-ranked vote. Such adjusted voting reduces (but not eliminates) the weighted votes for genotypes that are similar to the top-ranking allele, and thus give genetically less related alleles more weight. At the same time, similar alleles are not ignored. Ranking can be further refined by taking into consideration overall coverage and depth of coverage. For example, a first re-ranked allele may score higher with substantially lower overall coverage and depth of coverage than a second re-ranked allele. In such case, the second re-ranked allele may be more likely the correct allele. The top-ranking re-ranked allele is then the second allele for the same HLA-type. Of course, and as noted above, re-ranking may factor in overall coverage and depth of coverage, and may even lead to disqualification of an allele where the overall coverage and/or depth of coverage falls below a user defined threshold (e.g., overall coverage less than 94%, and/or depth of coverage less than 10×). In addition, using matching k-mers as a vote also allows identification of unique k-mers in a particular vote, which may serve as further guidance whether or not the particular vote is likely a correct prediction. Table 1 below provides an exemplary prediction of alleles for various HLA-types (HLA-A, HLA-B, HLA-C, DRB1, DQB1) using a de Bruijn graph approach and a single genome (YRI) from 1000 the Genomes Project (IGSR: The International Genome Sample Resource).

be appreciated that the % unique k-mers (relative to top ranking) also provides a good indication of similarity and distinguishing power of the systems and methods presented herein.

Of course, it should be appreciated that the analysis and HLA prediction need not be limited to the particular HLA-types shown above, but that all HLA-types and allelic variants are contemplated herein, including HLA-E, HLA-F, HLA-G, HLA-H, HLA-J, HLA-K, HLA-L, HLA-V, HLA-DQA1, HLA-DMA, HLA-DMB, HLA-DOA, HLA-DOB, HLA-DPA1, HLA-DPB1, HLA-DRA, HLA-DRB345, HLA-MICA, HLA-MICB, HLA-TAP1, HLA-TAP2, and even newly discovered HLA types and their corresponding alleles. Moreover, it should be appreciated that the analysis need not be limited to a single HLA-type, but that multiple HLA-types are suitable for use herein. Consequently, the reference sequence may include two, three, four, or more HLA-types, with a collection of alleles for the respective HLA-types. As each HLA-type has a significant number of alleles, it is contemplated that not all of the known alleles need to be included in the reference sequence. For example, the reference sequence may include alleles with an allele frequency above a particular threshold such as an allele frequency of at least 0.1%, or at least 0.5%, or at least 1%, or at least 2%, or at least 5%. Therefore, and viewed from a different perspective, suitable reference sequences may include at least 10, or at least 30, or at least 50, or at least 100, or at least 200 or at least 500, or even more different alleles for at least one HLA type.

Similarly, it should be appreciated that the nature and type of the patient sequence reads may vary considerably. For

TABLE 1

|  | Weighted Score | Unweighted Score | % Unique k-mers | Coverage Depth | Fraction Covered | Allele(s) |
| --- | --- | --- | --- | --- | --- | --- |
| NA19238 HLA-A | 23721 | 23721 | 1.000 | 21.9 | 0.925 | A*30:01:01 |
| NA19238 HLA-A | 15272 | 22197 | 0.269 | 20.5 | 0.925 | A*36:01 |
| NA19238 HLA-A | 3595 | 9609 | 0.014 | 11.9 | 0.938 | A*30:18 |
| NA19238 HLA-A | 2164 | 5211 | 0.031 | 9.8 | 0.970 | A*30:53 |
| NA19238 HLA-A | 1575 | 5504 | 0.087 | 10.3 | 0.944 | A*30:11:01 |
| NA19238 HLA-B | 17523 | 17523 | 1.000 | 16.3 | 0.921 | B*53:01:01 |
| NA19238 HLA-B | 15938 | 16485 | 0.709 | 15.3 | 0.913 | B*57:03:01 |
| NA19238 HLA-B | 5864 | 12275 | 0.000 | 11.4 | 0.921 | B*58:01:01 |
| NA19238 HLA-B | 4830 | 11329 | 0.000 | 12.9 | 0.926 | B*57:01:19 |
| NA19238 HLA-B | 1913 | 9496 | 0.000 | 8.8 | 0.921 | B*58:01:07 |
| NA19238 HLA-B | 762 | 4835 | 0.037 | 9.1 | 0.925 | B*35:27 |
| NA19238 HLA-B | 318 | 4899 | 0.000 | 9.2 | 0.976 | B*58:36 |
| NA19238 HLA-C | 28463 | 28463 | 1.000 | 26.2 | 0.924 | C*18:02 |
| NA19238 HLA-C | 18111 | 26189 | 0.317 | 24.1 | 0.924 | C*04:01:01:01, C*04:01:01:02, C*04:01:01:03, C*04:01:01:04, C*04:01:01:05, C*04:82 |
| NA19238 HLA-C | 4320 | 14117 | 0.011 | 17.5 | 0.927 | C*04:41 |
| NA19238 HLA-C | 728 | 3173 | 0.042 | 6.0 | 0.914 | C*04:34 |
| NA19238 DRB1 | 19990 | 19990 | 1.000 | 25.4 | 0.916 | DRB1*16:02:01 |
| NA19238 DRB1 | 17110 | 19954 | 0.599 | 25.4 | 0.914 | DRB1*11:01:02 |
| NA19238 DRB1 | 3119 | 6310 | 0.000 | 11.7 | 0.909 | DRB1*11:97 |
| NA19238 DRB1 | 2411 | 2790 | 0.655 | 10.9 | 1.000 | DRB1*15:96 |
| NA19238 DRB1 | 1278 | 4079 | 0.065 | 7.6 | 0.920 | DRB1*11:01:08 |
| NA19238 DRB1 | 893 | 2165 | 0.000 | 8.5 | 0.934 | DRB1*16:23 |
| NA19238 DQB1 | 17310 | 17310 | 1.000 | 22.4 | 0.930 | DQB1*06:02:01 |
| NA19238 DQB1 | 16390 | 16572 | 0.895 | 21.5 | 0.933 | DQB1*05:02:01 |

As can be readily seen from the exemplary analysis, the top-ranking HLA allele for each type is readily distinguished, with the second ranking allele being substantially distinct from the remaining alleles in the same HLA-type, particularly where the weighted score is observed. The choice of the first and second HLA alleles for each HLA-type is also well supported by the significantly higher coverage depth and to some degree coverage. It should also example, contemplated patient sequence reads will include DNA and RNA sequences, each of which may be obtained using all methods known in the art. Moreover, such sequence reads may be provided from a data storage (e.g., database) or from a sequencing equipment. For example, DNA sequence reads may be derived from an NGS sequencing machine, and RNA sequences may be derived from rtPCR sequencing devices. Thus, the length of the patient sequence reads will typically be longer than 20 bases, more typically longer than 50 bases, and most typically be longer than 100 bases, however, generally shorter than 5,000 bases, or shorter than 3,000 bases, or shorter than 1,000 bases. Consequently, contemplated patient sequence reads may have a length of between 100 and 500 bases or between 150 and 1,000 bases.

To reduce computing time and data storage and/or memory requirement, it is further preferred that the patient sequence reads will be preselected to genomic areas where HLA-type genes are located. For example, patient sequence reads that map to chromosome 6p21.3 are especially contemplated. Likewise, the patient sequence reads may also be selected on the basis of one or more annotations that indicate likely position to a genome where HLA allele loci are known. Alternatively, the annotation may also directly reference the likelihood of the sequence as being an HLA allele.

Regardless of the length of the patient sequence reads, it is generally preferred that the patient sequence reads are decomposed in k-mers having a relatively short length, and particularly preferred lengths will typically be between 10 and 30. Notably, such short k-mer length allows for a higher resolution and accuracy in variant calling, particularly due to the weighted vote for a fragment containing such k-mers. Thus, k-mer length is typically between 10-30, or between 15-35, or between 20-40. Viewed from a different perspective, k-mers will preferably have a length of less than 60, even more preferably less than 50, and most preferably less than 40, but longer than 5, more typically longer than 8, and most typically longer than 10. For example, suitable k-mers will therefore have a length of between 5% and 15% of a length of the patient sequence read.

With respect to ranking and the composite match score, it should be noted that in most preferred aspects a match score will be generated on the basis of all k-mers that are present in the patient sequence reads, and that each voting (i.e., matching) k-mer has identical voting power. As a result, a patient sequence read will have a specific quantitative read support for each of the alleles in the reference sequence. Moreover, as in most instances each position in the genome has a >1 sequencing depth, and as each patient sequence read will only cover a fraction of the full length of an allele, each allele may receive multiple votes from multiple patient sequence reads. Most typically, all of the votes for an allele are added to so arrive at a composite match score for that allele. The composite match score for each of the alleles is then used for ranking and further analysis.

However, in alternative aspects of the inventive subject matter, it should be noted that the scoring and calculation of a composite score may also be modified to achieve one or more specific purposes. For example, a match score for a fragment need not be calculated from all of the matching k-mers, but may count only a random number or selection of k-mers. On the other hand, k-mers with less than a perfect match (e.g., 14/15 matching) may be given voting rights, possibly with a lower voting weight. Likewise, and particularly where metadata are available, voting weight may be reduced for k-mers and/or patient sequence reads where read quality falls below a specific threshold. On the other hand, where low sequencing depth is present, votes may be over-represented for a particular fragment. In yet another contemplated aspect, especially where read depth is relatively high (e.g., at least 15×, or at least 20×, or at least 30×), patient sequence reads for the same position may be eliminated or included based on the vote. Consequently, the composite match score may be based on all of the available votes, or only upon a fraction of the votes available for an allele.

While ranking typically relies on the cumulative match score, it should be recognized that ranking may also be corrected using at least one factor. Such correcting factors include fraction covered, sequencing depth, amount of unique k-mers, and metadata of the fragments as available. For example, voting weight may be reduced for alleles where coverage of the allele is below a predetermined threshold (e.g., less than 96%, or less than 94%, or less than 92%, etc.) and/or where sequencing depth is below a predetermined threshold (e.g., less than 15×, or less than 12×, or less than 10×, etc.). On the other hand, voting weight may also be increased, for example, for alleles where the percentage of unique k-mers is above a predetermined threshold (e.g., above 2%, or above 5%, or above 10%).

The top ranked allele is typically the first predicted allele for a given HLA-type, while the second ranked allele may be the second allele for the same HLA-type. It should be noted, however, that the scoring may be further improved or refined as needed, particularly where many of the ranks following the top rank have similar composite match scores. (e.g., where a significant portion of their score comes from a highly shared set of k-mers). In one preferred example, a score refinement procedure may be implemented that includes a recalculation in which the weight of k-mers that matched (either perfectly, or with a similarity of at least 90%, or at least 95%, or at least 97%, or at least 99%) the top-ranking k-mer are reduced by a correction factor. Such correction factor can devalue a vote by any predetermined amount. Most typically the correction factor will devalue the vote by 10%, or 20-40%, or 40-60%, or even more. This has the effect of reducing the weighted votes for genotypes that are similar to the top-ranking allele, relatively making the genotypes that differ more important. Thus, it should be noted that the first allele is identified based on the highest most support from all sequencing data, while the second allele is identified in a more heuristics based approach, using both the raw weighted vote, scaled weighted vote, and the coverage to determine if the second allele has support in the datasets (e.g., high scaled weighted vote and genotype coverage) or if the genome is homozygous for the first genotype (e.g., high raw weighted vote, very low scaled weighted vote, no other alleles with decent coverage). Viewed from a different perspective, re-ranking advantageously allows more accurate differentiation of the second allele even in the presence of alleles similar to the top ranking allele. Moreover, such method also allows ready identification of homozygous HLA-types. In addition, it should be appreciated that such methods do not require the use of a hash table and allow identification of the proper HLA allele without assembling the sequence reads into the HLA type. Still further, contemplated systems and methods also allow for use of DNA and/or RNA data.

One typical embodiment of contemplated methods is exemplarily shown in FIG. 1 where method 100 has one step 110 in which a reference sequence is provided that includes a plurality of sequences of known and distinct HLA alleles. In step 120, a plurality of patient sequence reads are provided, wherein at least some of the patient sequence reads include a sequence encoding a patient specific HLA, while in step 130, the plurality of patient sequence reads is decomposed into a plurality of respective sets of k-mers (typically with each k-mer advancing in increments of 1 base (or less preferably 2 bases, or 3 bases, or 4 bases)). In step 140, a composite de Bruijn graph is generated using the reference sequence and the plurality of respective sets of k-mers, and in step 150, each of the known and distinct HLA alleles are ranked using a composite match score that is calculated from respective votes of the plurality of patient sequence reads, and wherein each vote uses k-mers that match corresponding segments in the known and distinct HLA alleles.

Figure 2:
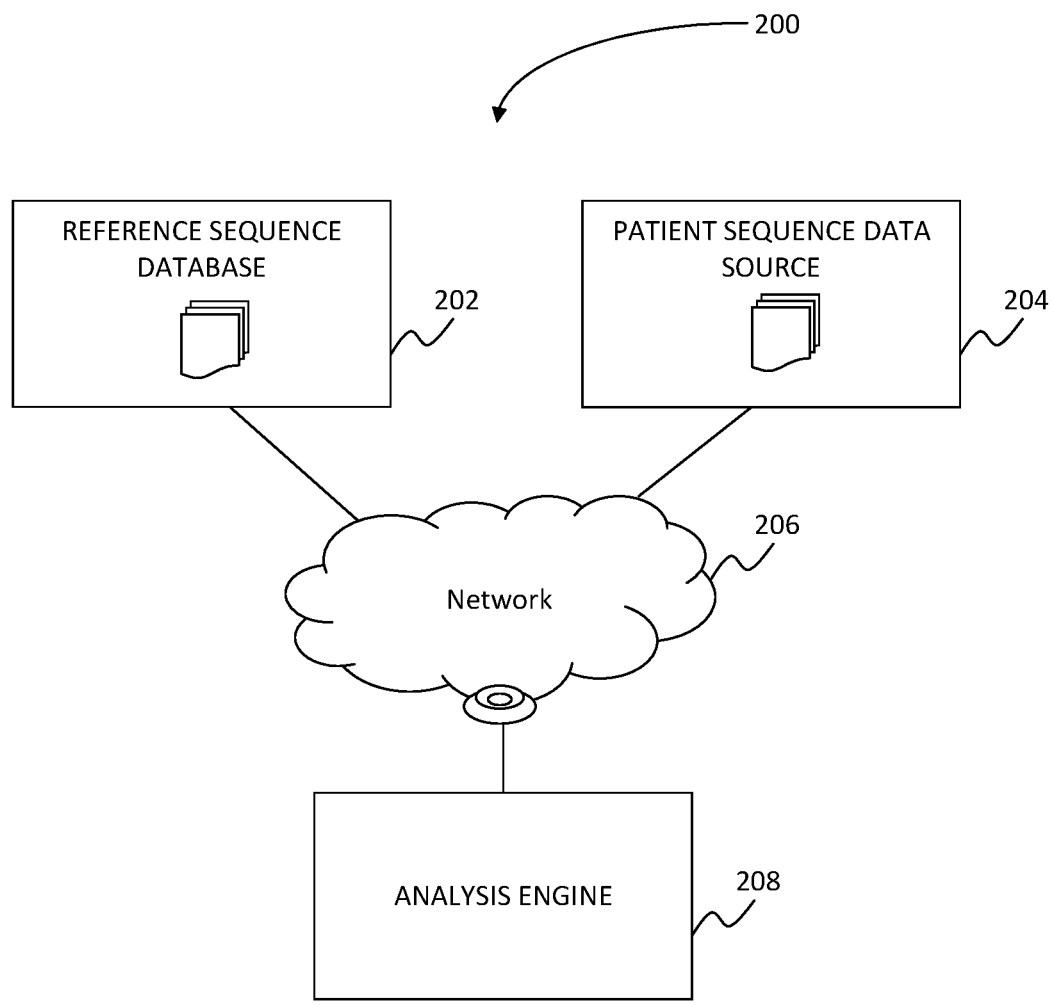
FIG. 2 is a schematic of one exemplary computer system according to the present inventive subject matter.

An exemplary system for such method is shown in FIG. 2 where the system 200 includes a reference sequence database 202 (e.g., database or file storing a reference sequence that includes a plurality of sequences of known and distinct HLA alleles) and also includes a patient sequence data source 204 (e.g., sequence database or sequencing device storing or providing a plurality of patient sequence reads, wherein at least some of the patient sequence reads include a sequence encoding a patient specific HLA), wherein both are informationally coupled via network 206 (e.g., LAN, WAN, Ethernet, Internet) to the analysis engine 208 that is programmed to (i) decompose the plurality of patient sequence reads into a plurality of respective sets of k-mers; (ii) generate a composite de Bruijn graph using the reference sequence and the plurality of respective sets of k-mers; and (iii) rank each of the known and distinct HLA alleles using a composite match score that is calculated from respective votes of the plurality of patient sequence reads, and wherein each vote uses k-mers that match corresponding segments in the known and distinct HLA alleles.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

Moreover, it should be noted that the systems and methods presented herein improve computer function as structuring and ranking of de Bruijn graph elements (and weighting) vastly increases accuracy and speed as compared to traditional data formats and processing schemes. Furthermore, it must be appreciated that the problem solved by the inventor is specific to the field of bioinformatics and would not even exist without computing of omics information. Finally, it should be recognized that the tasks performed by the analysis engine cannot be reasonably performed within the lifetime of a human without aid of computer systems.

As can be readily seen from the above, contemplated systems and methods provide for each HLA type a top score that is substantially higher rated/weighted as the second place score. Thus, it should be recognized that based on a De Bruijn graph-type analysis, HLA-types can be predicted with very high accuracy. Moreover, it should be recognized that the systems and methods presented herein are also suitable for various other tasks such as typing of pathogens (e.g., viral pathogens such as HPV, bacterial pathogen such as myobacteria, or parasitic pathogens such as *Plasmodium falciparum*) where the pathogen variants form part of the reference sequence, or typing of tumor diversity, etc.

In a further aspect of the inventive subject matter, contemplated system and methods based on de Bruijn graphs may also be employed to identify and classify structural variants. Here, reference and raw sequencing data are obtained from two genomic regions (e.g., the two sides of putative structural variations, for example, bcr-abl fusion) and are used to build the graph. Bubbles are then identified as possible structural variations where bounding reference edges are separated beyond a user-defined minimum genomic distance or where the bounding reference edges are located on different chromosomes. While such approach requires in most cases a priori positional knowledge of the suspected structural variation (positions of the reference edges provide the precise locations in the genome where a structural variation is suspected), such knowledge does generally not help identify the exact sequence at the boundaries. Using the De Bruijn graph approach now allows for a much more precise reconstruction of the structural variation and helps any novel sequence near or within the breakpoint. It should be noted that such methods will work not only where the structural variations (e.g., insertions, duplication, etc.) are located on the same strand, but will also be equally useful to identify inversions where construction of the graph also includes use of calculated reverse complement k-mers. As already noted earlier, the so identified structural variations can then be reported in a vcf or other suitable format.

For example, collected sequence information from a tumor may be represented in a colored De Bruijn graph where the edges are k-mers (e.g., k=15) having "colors" that identify which input source the k-mer is found in (e.g., reference, normal sample, and/or tumor sample, samples taken at different times or ages, samples from different patient or subject groups, etc.), and where each edge is connected to adjacent edges. Of course, it should be noted that the sequences can be DNA as well as RNA sequences, which advantageously allows for identification of expressed somatic mutations, RNA editing and alternate splicing (e.g., where DNA and RNA are from the same tissue). Most typically, in one preferred aspect of the inventive subject matter, a first graph is constructed from a reference sequence to store k-mer positions in a genome. Preferably, and depending on the particular task required, the k-mers will have a length of between 3 and 300 bases, more preferably between 10-100 bases. For example, where indel analysis is desired, k-mer lengths may be between 20-50 (e.g., k=30). Thus, and viewed from another perspective, the k-mer length may be between 5% to 15% of the average length of sequence reads. Once the first graph is established, k-mers from tumor and normal raw sequencing data located in a given region of genome (including unmapped anchored reads) are added. As needed, weak edges can be pruned from the graph to remove reads for which maximal support is below a specific user defined threshold (e.g., where k=13, threshold is 8). Such pruning will typically increase accuracy of the sequence prediction/alignment.

Example data structures for two adjoining edges within a de Bruijn graph (k=5) are described below:

---

Edge0.sequence = ATATC
Edge0.outgoing = [TATCG, TATCC]
Edge0.incoming = [TATAT]

-continued

```
Edge0.support = {'reference': 1, 'tumor': T0, 'normal': N0}
Edge0.quality_sum = {'tumor': TQ0, 'normal': NQ0}
Edge1.sequence = TATCG
Edge1.outgoing = [ATCGG]
Edge1.incoming = [ATATC]
Edge1.support = {'reference': 0, 'tumor': T1, 'normal': N1}
Edge1.quality_sum = {'tumor': TQ1, 'normal' : NQ1}
```

In this example, the Edge0 data structure has two outgoings edges defined by their kmer sequences TATCG and TATCC, the former of which is described in the subsequent Edge1 data structure. Edge1's incoming edge links back to Edge0. The support listed in the above data structure summarizes the number of times the edge's sequence was seen in the sequencing data ('tumor' or 'normal') or the reference genome ('reference'). Based on the support in the above edges, Edge0 has support in the reference genome while the outgoing edge it is connected to (Edge1) does not. This indicates that Edge1 could be the beginning of a non-reference variant, but further introspection of the subsequent edges is necessary to determine if its topology is consistent with a true variant (e.g. a "bubble" in the de Bruijn graph caused by a SNV or small insertion/deletion that is bounded by edges present in the reference genome) or an artefactual variant (e.g. a "tip" in the graph that does not reconnect to an edge in the reference genome, potentially caused by junk or random sequencing data). Depending on the level of support in the 'tumor' and 'normal' sequencing data (e.g. T0, N0, T1, and N1), the somatic or germline classification of the non-reference variant can be determined. In one simple method of classification, a variant would be classified as germline if T1>0 and N1>0, somatic if T1>0 and N1=0, or LOH if T1=0 and N1>0, but in almost all practical incarnations, the somatic or germline status would be determined via a summary analysis of the entire path describing the non-reference variant (i.e. average/minimum/maximum support and base quality of edges within the non-reference path).

In a further step, the so constructed composite graph is then analyzed for junctions at which tumor and reference diverge. For each divergence, a depth-first search is employed to identify all unique paths through tumor edges that result in tumor converging with reference, which is commonly shown as a bubble in a de Bruijn graph. Breadcrumbs can be used to avoid loops. The composite graph is then established with additional sequences. Here, one sequence may represent matched normal tissue of the same patient from which two other sequences are obtained, tumor DNA and tumor RNA. In such example, tumor DNA and tumor RNA are identical (which is not necessarily always the case). Points of divergence and convergence are driven by the differences in sequence information using the k-mers. As indicated above, the area of divergence produces a 'bubble' in the graph. Thus, and viewed from another perspective, is should be appreciated that the tumor sequence may have both a point of divergence and a point of re-convergence. As should also be noted, tumor DNA and RNA graphs may parallel each other, which indicates sequence identity of the DNA and its corresponding transcript.

Statistical analysis from the end of each bubble solution can then be employed to identify the most likely alignment and/or sequence. As in most typical embodiments the sequences are not mere raw sequence reads but annotated SAM or BAM files, statistical analysis can include read specific parameters based on the metadata for each read. Therefore, statistical analysis may include maximal support, mapping/base qualities for k-mers, support in the matched-normal, etc. As a result, it should be recognized that backtracking along reference edges to reconstruct the reference sequence and determination of location in the genome can be performed for paths in the graph that meet typically user defined criteria (e.g., min support >X reads, max support in normal <Y reads, etc.). So reconstructed sequences and/or structures can then be used to classify the specific variant. Preferably, the variant classification is presented in a vcf format, although other formats are also contemplated.

Example

To validate HLA prediction, three independent known patient records and samples were obtained from the 1000 Genome project (NA19238, NA19239, and NA19240) and HLA-types were then predicted as discussed above. Remarkably and unexpectedly, HLA determination and prediction using De Bruijn graph method as described above had near perfect matches with the exception for HLA-C (for NA19238), DRB1 (for NA19239), and HLA-C (for NA19240) as can be seen in the Tables 2A and 2B below.

TABLE 2A

| | | | Predictions | | | | |
|---|---|---|---|---|---|---|---|
| NA19238 | HLA-A | 23721 | 23721 | 1.000 | 21.9 | 0.925 | A*30:01:01 |
| NA19238 | HLA-A | 15272 | 22197 | 0.269 | 20.5 | 0.925 | A*36:01 |
| NA19238 | HLA-B | 17523 | 17523 | 1.000 | 16.3 | 0.921 | B*53:01:01 |
| NA19238 | HLA-B | 15938 | 16485 | 0.709 | 15.3 | 0.913 | B*57:03:01 |
| NA19238 | HLA-C | 28463 | 28463 | 1.000 | 26.2 | 0.924 | C*18:02 |
| NA19238 | HLA-C | 18111 | 26189 | 0.317 | 24.1 | 0.924 | C*04:01:01 |
| NA19238 | DRB1 | 19990 | 19990 | 1.000 | 25.4 | 0.916 | DRB1*16:02:01 |
| NA19238 | DRB1 | 17110 | 19954 | 0.599 | 25.4 | 0.914 | DRB1*11:01:02 |
| NA19238 | DQB1 | 17310 | 17310 | 1.000 | 22.4 | 0.930 | DQB1*06:02:01 |
| NA19238 | DQB1 | 16390 | 16572 | 0.895 | 21.5 | 0.933 | DQB1*05:02:01 |
| NA19239 | HLA-A | 24093 | 24093 | 1.000 | 22.2 | 0.926 | A*02:01:01 |
| NA19239 | HLA-A | 17596 | 20701 | 0.537 | 19.1 | 0.927 | A*68:02:01 |
| NA19239 | HLA-B | 21308 | 21308 | 1.000 | 19.8 | 0.918 | B*35:01:01 |
| NA19239 | HLA-B | 15080 | 20254 | 0.286 | 18.8 | 0.912 | B*52:01:02 |
| NA19239 | HLA-C | 18529 | 18529 | 1.000 | 17.0 | 0.920 | C*04:01:01 |
| NA19239 | HLA-C | 17846 | 18484 | 0.707 | 17.0 | 0.919 | C*16:01:01 |
| NA19239 | DRB1 | 26014 | 26014 | 1.000 | 33.1 | 0.914 | DRB1*13:01:01 |
| NA19239 | DRB1 | 16174 | 24412 | 0.178 | 31.0 | 0.914 | DRB1*12:01:01 |
| NA19239 | DQB1 | 18503 | 18503 | 1.000 | 24.6 | 0.930 | DQB1*05:01:01 |
| NA19239 | DQB1 | 13459 | 13510 | 0.939 | 17.5 | 0.931 | DQB1*03:01:01 |

TABLE 2A-continued

| | | | Predictions | | | | |
|---|---|---|---|---|---|---|---|
| NA19240 | HLA-A | 21944 | 21944 | 1.000 | 20.2 | 0.924 | A*30:01:01 |
| NA19240 | HLA-A | 20059 | 20512 | 0.800 | 18.9 | 0.929 | A*68:02:01 |
| NA19240 | HLA-B | 18637 | 18637 | 1.000 | 17.3 | 0.927 | B*35:01:01 |
| NA19240 | HLA-B | 17850 | 18550 | 0.682 | 17.3 | 0.926 | B*57:03:01 |
| NA19240 | HLA-C | 28054 | 28054 | 1.000 | 25.8 | 0.923 | C*18:02 |
| NA19240 | HLA-C | 20132 | 27609 | 0.390 | 25.3 | 0.919 | C*04:01:01 |
| NA19240 | DRB1 | 22869 | 22869 | 1.000 | 29.1 | 0.917 | DRB1*16:02:01 |
| NA19240 | DRB1 | 17094 | 20016 | 0.591 | 25.4 | 0.915 | DRB1*12:01:01 |
| NA19240 | DQB1 | 14654 | 14654 | 1.000 | 19.0 | 0.930 | DQB1*05:02:01 |
| NA19240 | DQB1 | 10926 | 10959 | 0.951 | 14.2 | 0.931 | DQB1*03:01:01 |

TABLE 2B

| | Truth: | |
|---|---|---|
| NA19238 | HLA-A | A*30:01 |
| NA19238 | HLA-A | A*36:01 |
| NA19238 | HLA-B | B*53:01 |
| NA19238 | HLA-B | B*57:03 |
| NA19238 | HLA-C | C*18:01 |
| NA19238 | HLA-C | C*04:01 |
| NA19238 | DRB1 | DRB1*16:02 |
| NA19238 | DRB1 | DRB1*11:01 |
| NA19238 | DQB1 | DQB1*06:02 |
| NA19238 | DQB1 | DQB1*05:02 |
| NA19239 | HLA-A | A*02:01 |
| NA19239 | HLA-A | A*68:02 |
| NA19239 | HLA-B | B*35:01 |
| NA19239 | HLA-B | B*52:01 |
| NA19239 | HLA-C | C*04:01 |
| NA19239 | HLA-C | C*16:01 |
| NA19239 | DRB1 | DRB1*13:01 |
| NA19239 | DRB1 | DRB1*13:01 |
| NA19239 | DQB1 | DQB1*05:01 |
| NA19239 | DQB1 | DQB1*03:01 |
| NA19240 | HLA-A | A*30:01 |
| NA19240 | HLA-A | A*68:02 |
| NA19240 | HLA-B | B*35:01 |
| NA19240 | HLA-B | B*57:03 |
| NA19240 | HLA-C | C*15:01 |
| NA19240 | HLA-C | C*04:01 |
| NA19240 | DRB1 | DRB1*16:02 |
| NA19240 | DRB1 | DRB1*12:01 |
| NA19240 | DQB1 | DQB1*05:02 |
| NA19240 | DQB1 | DQB1*03:01 |

Here, ambiguous digits were removed from the above alleles. For example, if predictions were A*04:02:01 and A*04:02:02, the last ambiguous digit (here: 01 or 02) was removed and so yielded prediction A*04:02. A further investigation into the differences between the predicted HLA types and the experimentally determined HLA types ('truth') surprisingly revealed that the experimentally determined HLA was inconsistent with the expected inheritance pattern, as NA19238 and NA19239 were the parents of NA19240 as is discussed in more detail below.

With respect to "Truth" being determined C*18:01 and Predicted C*18:02, it is noted that there is only a single base change between the two allele forms. Notably, C*18:01 has a sequence of CTGGTTGTC (relevant sequence portion only) with zero read support in the WGS data, while C*18:02 has a sequence of CTGGCTGTC (relevant sequence portion only) with 33 reads supporting it in the WGS data. According to the data, there is no support for "Truth" C*18:01, while there is lots of support for the Predicted C*18:02.

With respect to "Truth" being determined DRB1*13:01 and Predicted DRB1*12:01: it is noted that NA19240 is the child of parents NA19238 and NA19239. As children inherit only one allele for each HLA type from each parent, the true allele can be determined from simple basic Mendelian inheritance:

| Parent 1 (NA19238): | 16:02, | 11:01 | |
| Parent 2 (NA19239): | 13:01, | ? | <- The allele in question |
| Child (NA19240): | 16:02, | 12:01 | |

As can be seen from the above, the child must inherit 16:02 from Parent 1, which means that allele 12:01 must come from Parent 2. Notably, "Truth" lists the second allele for Parent 2 as 13:01, but this is impossible based on inheritance. The Predicted allele for Parent 2 is 12:01. However, this is exactly what one would expect based upon inheritance. Consequently, and based on the cases above, the "incorrect" predictions were actually due to errors in "Truth". Thus, the HLA prediction method presented herein has demonstrated 100% accuracy across a diverse panel of 5 HLAs in 3 individual datasets. It should be further appreciated that the above prediction was performed using average coverage WGS samples. The accuracy of the method can be even further much improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Moreover, contemplated methods are very fast (with run times typically less than 5 min) to obtain predictions on all 26 HLA types, and newly discovered or extremely rare HLA alleles can be added in a trivial manner. Lastly, it should be noted that no population-based heuristics are required to produce accurate results.

Thus, it should be appreciated that the systems and methods presented herein may be used to validate or confirm diff objects found in genome analysis. Moreover, where RNA information is used in the same graph, mutant allele expression may be immediately identified. Still further, and based on the results and discussion above, it is also contemplated that the systems and methods will be capable of calling gene fusions using RNA-Seq, especially "actionable fusions" (e.g. BCR-ABL) or oncogenic gene isoforms (e.g. EGFRvIII).

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Moreover, groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An in silico method of predicting an HLA-type for a patient, comprising:
   generating a plurality of patient sequence reads from a tissue sample of the patient, wherein at least some of the patient sequence reads include a sequence encoding a patient specific HLA, wherein the plurality of patient sequence reads includes the whole genome sequence;
   decomposing the plurality of patient sequence reads into a plurality of respective sets of k-mers;
   generating a composite de Bruijn graph using the plurality of respective sets of k-mers, and a reference sequence that includes a plurality of sequences of known and distinct HLA alleles;
   ranking each of the known and distinct HLA alleles using a composite match score that is calculated from respective votes of the plurality of patient sequence reads, and wherein each vote uses k-mers that match corresponding segments in the known and distinct HLA alleles;
   identifying a top ranked HLA allele as the first HLA-type of the patient; and
   re-ranking remaining non-top-ranking known and distinct HLA alleles using an adjusted composite match score to identify an adjusted top-ranking HLA allele as the second HLA type of the patient.

2. The method of claim 1 wherein the reference sequence includes at least one of alleles for at least one HLA type that have an allele frequency of at least 1%, at least ten different alleles for at least one HLA type, and alleles for at least two distinct HLA types.

3. The method of claim 1 wherein the HLA type is an HLA-A type, an HLA-B type, an HLA-C type, a HLA-DRB-1 type, and/or a HLA-DQB-1 type.

4. The method of claim 1 wherein the patient sequence reads are next generation sequencing reads and further comprise metadata.

5. The method of claim 1 wherein the patient sequence reads have a length of between 50 and 250 bases.

6. The method of claim 1 wherein the k-mers have a length of 10-20 or a length of between 5% and 15% of a length of the patient sequence read.

7. The method of claim 1 wherein the composite match score is a sum of all votes from the plurality of patient sequence reads, wherein the vote is a value representing a fraction of matching k-mers to total number of k-mers per patient sequence read.

8. The method of claim 1 wherein the adjusted composite match score is calculated from respective adjusted votes of the plurality of patient sequence reads; and
   wherein the adjusted votes are calculated by devaluing a weight of a k-mer that matches the first HLA-type.

9. A computer system for in silico predicting an HLA-type for a patient, comprising:
   a patient sequence data source storing or generating a plurality of patient sequence reads from a tissue sample of the patient, wherein at least some of the patient sequence reads include a sequence encoding a patient specific HLA, wherein the plurality of patient sequence reads includes the whole genome sequence;
   an analysis engine, programmed to
   (i) decompose the plurality of patient sequence reads into a plurality of respective sets of k-mers;
   (ii) generate a composite de Bruijn graph using the plurality of respective sets of k-mers, and a reference sequence that includes a plurality of sequences of known and distinct HLA alleles;
   (iii) rank each of the known and distinct HLA alleles using a composite match score that is calculated from respective votes of the plurality of patient sequence reads, and wherein each vote uses k-mers that match corresponding segments in the known and distinct HLA alleles;
   (iv) identifying a top ranked HLA allele as the first HLA-type of the patient; and
   (v) re-ranking remaining non-top-ranking known and distinct HLA alleles using an adjusted composite match score to identify an adjusted top-ranking HLA allele as the second HLA-type of the patient.

10. The computer system of claim 9 wherein the reference sequence includes alleles for at least one HLA type that have an allele frequency of at least 1%, or wherein the reference sequence includes at least ten different alleles for at least one HLA type, or wherein the reference sequence includes alleles for at least two distinct HLA types.

11. The computer system of claim 9 wherein the HLA type is an HLA-A type, an HLA-B type, an HLA-C type, a HLA-DRB-1 type, and/or a HLA-DQB-1 type.

12. The computer system of claim 9 wherein the patient sequence reads are next generation sequencing reads and further comprise metadata, or wherein the patient sequence reads have a length of between 50 and 250 bases.

13. The computer system of claim 9 wherein the k-mers have a length of 10-20, or wherein the k-mers have a length of between 5% and 15% of a length of the patient sequence read.

14. The computer system of claim 9 wherein the composite match score is a sum of all votes from the plurality of patient sequence reads, and wherein the vote is a value representing a fraction of matching k-mers to total number of k-mers per patient sequence read.

15. The computer system of claim 9 wherein the adjusted composite match score is calculated from respective adjusted votes of the plurality of patient sequence reads; and
   wherein the adjusted votes are calculated by devaluing a weight of a k-mer that matches the first HLA-type.

16. A non-transient computer readable medium containing program instructions for causing a computer system in which a reference sequence database and a patient sequence data source are informationally coupled to an analysis engine to perform a method comprising the steps of:
- generating, from patient sequence data source, to the analysis engine a plurality of patient sequence reads from a tissue sample of the patient, wherein at least some of the patient sequence reads include a sequence encoding a patient specific HLA, wherein the plurality of patient sequence reads includes the whole genome sequence;
- decomposing, by the analysis engine, the plurality of patient sequence reads into a plurality of respective sets of k-mers;
- generating, by the analysis engine, a composite de Bruijn graph using the plurality of respective sets of k-mers, and a reference sequence that includes a plurality of sequences of known and distinct HLA alleles;
- ranking, by the analysis engine, each of the known and distinct HLA alleles using a composite match score that is calculated from respective votes of the plurality of patient sequence reads, and wherein each vote uses k-mers that match corresponding segments in the known and distinct HLA alleles;
- identifying a top ranked HLA allele as a first HLA-type of the patient; and
- re-ranking remaining non-top-ranking known and distinct HLA alleles using an adjusted composite match score to identify an adjusted top-ranking HLA allele as a HLA type of a second allele of the patient.

17. The computer readable medium of claim 16 wherein the reference sequence includes alleles for at least one HLA type that have an allele frequency of at least 1%, or wherein the reference sequence includes at least ten different alleles for at least one HLA type, or wherein the reference sequence includes alleles for at least two distinct HLA types.

18. The computer readable medium of claim 16 wherein the k-mers have a length of 10-20, or wherein the k-mers have a length of between 5% and 15% of a length of the patient sequence read.

19. The computer readable medium of claim 16 wherein the composite match score is a sum of all votes from the plurality of patient sequence reads, and wherein the vote is a value representing a fraction of matching k-mers to total number of k-mers per patient sequence read.

20. The computer readable medium of claim 16 wherein the adjusted composite match score is calculated from respective adjusted votes of the plurality of patient sequence reads; and wherein the adjusted votes are calculated by devaluing a weight of a k-mer that matches the first HLA-type.

* * * * *